United States Patent
Brown

(10) Patent No.: US 6,365,798 B1
(45) Date of Patent: Apr. 2, 2002

(54) METHOD FOR ENHANCEMENT OF NATURALLY OCCURRING CYTOPLASMIC MALE STERILITY AND FOR RESTORATION OF MALE FERTILITY AND USES THEREOF IN HYBRID CROP PRODUCTION

(75) Inventor: Gregory G. Brown, Montréal (CA)

(73) Assignee: McGill University, Montreal (CA)

(*) Notice: Subject to any disclaimer, the term of this patent is extended or adjusted under 35 U.S.C. 154(b) by 0 days.

(21) Appl. No.: 09/447,303

(22) Filed: Nov. 23, 1999

Related U.S. Application Data

(63) Continuation of application No. PCT/CA98/00522, filed on May 26, 1998.
(60) Provisional application No. 60/047,795, filed on May 30, 1997.

(51) Int. Cl.[7] .............................. A01H 5/00; A01H 1/02; C12N 5/04; C12N 5/29; C12N 15/82
(52) U.S. Cl. .................. 800/274; 800/278; 800/287; 800/298; 800/306; 800/290; 435/468; 435/320.1; 435/430
(58) Field of Search ................................ 800/290, 288, 800/278, 274, 287, 298, 306; 435/410, 468, 320.1, 470; 536/23.6

(56) References Cited

U.S. PATENT DOCUMENTS

| | | | |
|---|---|---|---|
| 5,866,782 A | * | 2/1999 | Iwabuchi et al. |
| 5,914,447 A | * | 6/1999 | Araya et al. |

FOREIGN PATENT DOCUMENTS

| | | |
|---|---|---|
| EP | 06 75198 A | 10/1995 |
| WO | WO 90 08830 A | 8/1990 |
| WO | WO 92 05251 A | 4/1992 |
| WO | WO 94 18334 A | 8/1994 |

OTHER PUBLICATIONS

Dewey et al, 1986. Novel recombinations in the maize mitochondrial genome produce a unique transcriptional unit in the Texas male–sterile cytoplasm. Cell 44:439–449.*
Young et al, 1987. A fused mitochondrial gene associated with cytoplasmic male sterility is developmentally regulated. Cell 50:41–49.*
Moneger et al, 1994. Nuclear restoration of cytoplasmic male sterility in sunflower is associated with the tissue–specific regulation of a novel mitochondrial gene. EMBO J. 13:8–17.*
Schnable et al, 1998. The molecular basis of cytoplasmic male sterility and fertility restoration. Trends in Plant Science 3:175–180.*
Bonen et al, 1988. Triticum aestivum F1F0–ATPase precursor (atp6) gene, complete cds; mitochondrial gene for mitochondrial product. GenBank Accession No. M24084.*
Handa et al, 1992. RNA editing of atp6 transcripts from male–sterile and normal cytoplasms of rapeseed (*Brassica napus* L.). FEBS Let. 310:111–114.*
L'Homme et al, 1997. Brassica nap cytoplasmic male sterility is associated with expression of a mtDNA region containing a chimeric gene similar to the pol CMS–associated orf224 gene. Curr. Genet. 31:325–335.*
Tingdong et al, 1990. Studies on "Three Line" Polima Cytoplasmic Male Sterility Developed in *Brassica napus* L. Plant Breed. 104:115–120.*
Fan et al, 1986. Influence of temperature on sterility of two cytoplasmic male–sterility systems in rape (*Brassica napus* L.) Can. J. Plant Sci. 66:221–227.*
Singh, M. P. and Brown, G.G. (1991). The Plant Cell 3, 1349–1362.
Bonen, L. and Brown, G.G. (1993). Can J. Bot. 71, 645–660.
Stahl R. et al. (1994) Nucleic Acids Res 22, 2109–2113.
Hernould, M. et al. (1993). Proc. Natl. Acad. Sci. U.S.A. 90, 2370–2374.
van der Leegt–Plegt, L.M. et al. (1992). Plant Cell Reports 11, 20–24.
Jack, T. et al. (1994) Cell 76, 703–716.
Moloney, M. et al. (1989). Plant Cell Rep. 8, 238–242.
He, S. et al. (1996). Proc. Natl. Acad. Sci. U.S.A. 93, 11763–11768.
Chaumont, F. et al. (1995). Proc. Natl. Acad. Sci. USA 92, 1167–1171.
Wintz H. et al. (1995). Plant Mol Biol 28, 83–92.
Arnison P. et al., The PBI Bulletin, Jan. 1997, 1–11.
Wang, H.–M–, et al. (1995), Plant Molecular Biology 27, 801–807.
L'Homme, Y., et al. (1993), Nucleic Acids Research 21, 1903–1909.
Iwabuchi, M., et al. (1993), Embo Journal 12, No. 4, 1437–1446.
Biological Abstracts 103, Abstract No. 005999, Blanc V et al.

* cited by examiner

Primary Examiner—David T. Fox
Assistant Examiner—Anne Kubelik
(74) Attorney, Agent, or Firm—Susan Tandan; Swabey Ogilvy Renault

(57) ABSTRACT

The present invention relates to methods for enhancement of naturally occurring cytoplasmic male sterility and for restoration of male fertility and uses thereof in hybrid crop production. There is also disclosed a method for restoration of male fertility to cytoplasmic male sterile plants; which comprises the steps of: a) introducing into the nucleus of a plant cell a gene construct essentially consisting of a sequence encoding a mitochondrial transit peptide fused upstream of and in frame with an edited form of a normal mitochondrial gene that is co-transcribed with an unusual CMS–associated mitochondrial gene; b) selecting for plant cells that have acquired the gene construct in step a); and c) inducing regeneration of selected plant cells to produce a mature plant.

10 Claims, 5 Drawing Sheets

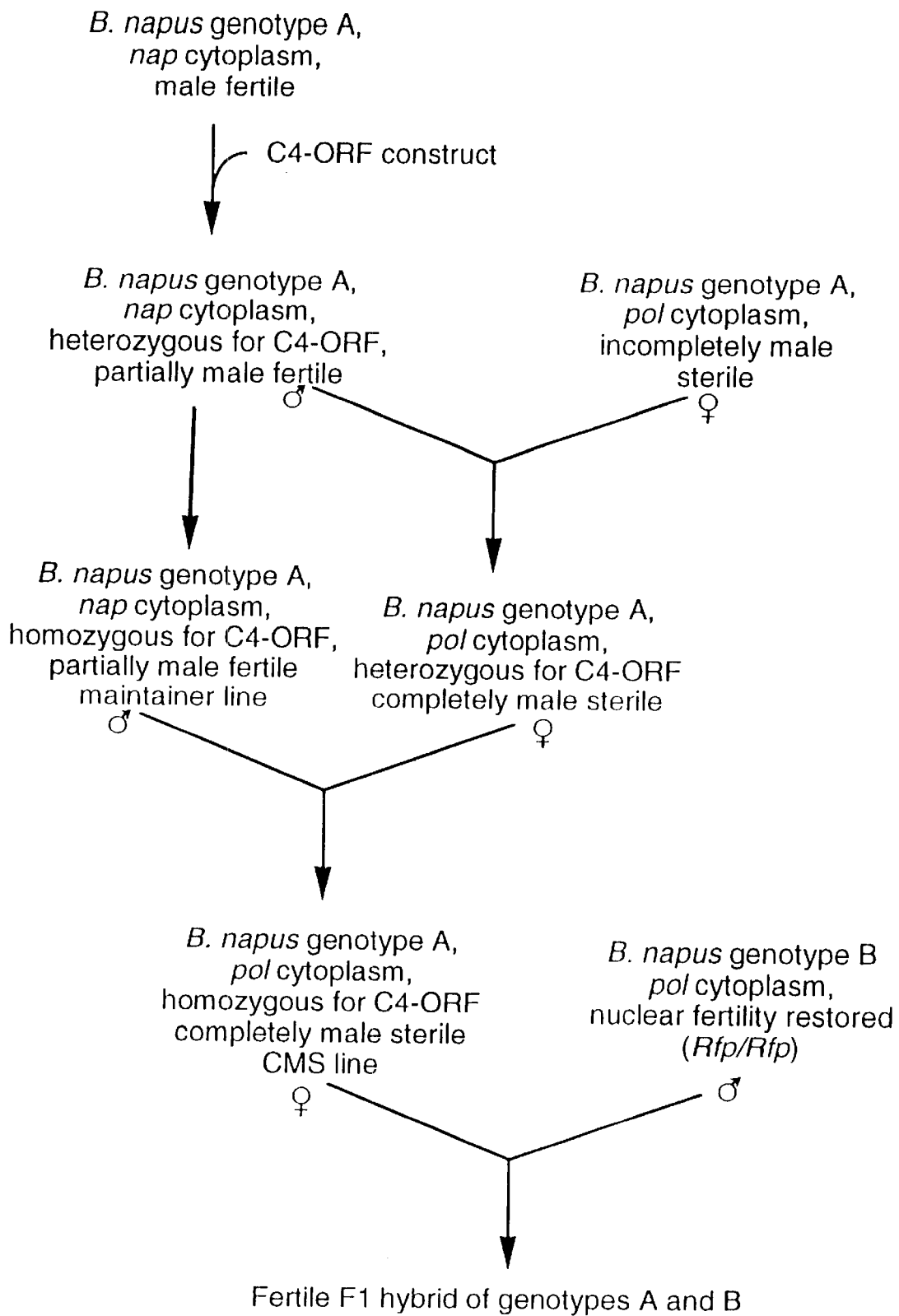

METHOD FOR ENHANCEMENT OF NATURALLY OCCURRING CYTOPLASMIC MALE STERILITY AND FOR RESTORATION OF MALE FERTILITY AND USES THEREOF IN HYBRID CROP PRODUCTION

This application is a continuation of PCT/CA98/00522 filed May 26, 1998 designating the United States and claiming priority of U.S. provisional Patent Application Ser. No. 60/047,795 filed May 30, 1997.

BACKGROUND OF THE INVENTION (a) Field of the Invention

The invention relates to methods for enhancement of naturally occurring cytoplasmic male sterility and for restoration of male fertility and uses thereof in hybrid crop production.

(b) Description of Prior Art

For many crops, hybrids, formed by crossing two or more different strains, provide higher yields than do the parental strains themselves. For example, in canola (*Brassica napus, campestris*), Canada's most important crop, manually produced hybrids have yields that can be up to 50% greater than those of the parental lines. This phenomenon, termed hybrid vigor, has been most successfully applied in maize (*Zea mays*). Hybrid maize constitutes approximately 90% of the North American crop.

To produce hybrid seed on a commercial scale, it is necessary to prevent self-pollination of the seed parent of the hybrid cross. This is a relatively simple matter in maize, because the male or pollen-producing organs (the stamens) are located in a different part of the plant than the female, or seed-bearing organs (the carpels), and the stamens, which collectively form a structure called the tassel, can easily be removed manually from the large numbers of plants used in a seed production operation. By contrast, in most crop species, such as canola, the stamens and carpels are located in the same floral structure, and manual emasculation of large numbers of plants is not possible. Hence, seed producers require alternative methods of pollination control for producing hybrids in these crops. A review of the technology developed for this purpose can be found in The PBI Bulletin article of Arnison P. (Arnison P. et al., The PBI Bulletin, January 1997, 1–11).

One alternative method is to use chemicals, called gametocides, that specifically kill pollen. These chemicals are generally expensive and are often only partially effective. For most crops, especially those like canola that flower over an extended period, this type of pollination control is not cost-effective. Nearly all hybrid seed production systems, therefore, rely on genetic control of pollination. Genetic pollination control mechanisms fall into three categories: self-incompatibility, "molecular hybridization" methods, and cytoplasmic male sterility.

Self incompatibility (SI) results from the capacity of some plants to reject their own pollen. Plants expressing SI can be used as the female line in hybrid production, but, because these plants normally reject their own pollen, it is usually difficult, and cost-ineffective, to propagate or maintain such lines. In addition, self-incompatibility is not found in most plant species. Molecular hybridization methods are the most recently developed. They rely on genetically engineered male sterility, caused by the specific expression of toxic proteins in pollen forming cells. Such introduced toxin genes act as dominant male sterility genes and can be used to generate female lines for hybrid seed production. As with SI, the propagation of such female lines is not straightforward and involves loss of plant material. The usefulness of these methods is still unclear, and at present they are used in the production of only a few hybrid varieties which are not widely grown.

Cytoplasmic male sterility (CMS), is a widespread and classic non-Mendelian trait. CMS plants are incapable of self-pollination and hence when a CMS line is planted alongside a male-fertile line, all the seed that forms on the sterile plants will be a hybrid of the two parents. Unlike most traits, CMS is maternally transmitted, i.e., it is passed on to offspring only through the seed parent. This property results from the fact that the gene or genes that determine CMS are located on mitochondrial DNA (mtDNA). Unlike most genes, which reside in nuclear DNA, genes in mtDNA are transmitted solely through the female in most plant species. As a result of this property of maternal transmission, it is possible to easily propagate female CMS lines, by pollinating with a male fertile "maintainer" line, that is identical to the CMS line in its nuclear genes, but which is male fertile because it lacks the CMS-causing mtDNA. However, again as a result of the maternal transmission of CMS, hybrid plants produced using female CMS lines would also be male sterile because they would carry the male-sterility conferring mtDNA. This is problematic for seed crops such as maize and canola, which require pollen production for the formation of seed, the harvested product. Fortunately, in many crop species, specific dominant nuclear genes termed restorers of fertility (Rf) have been identified that can suppress the male-sterile phenotype and "restore" fertility to F1 hybrids. The components of a CMS system, therefore, consist of the CMS line (which contains the male sterile (S) cytoplasm (or mtDNA) and is homozygous for the recessive or maintainer allele of the restorer gene), the maintainer line (which contains a fertile or normal mtDNA (F) but is isogenic with the CMS line at nuclear genetic loci), and the restorer line (which usually contains the male sterile mtDNA but is homozygous for the dominant nuclear Rf gene). The use of these components in a hybrid seed production scheme is illustrated in FIG. 1.

To produce a diverse set of hybrids using CMS, adequate numbers of restorer lines, that contain Rf genes, as well as "maintainer" lines, that are sterilized by the CMS mtDNA, must be available. The development of these lines through conventional genetics is a slow process that minimally requires several years of effort. For example, to develop a new restorer line it is necessary to first cross the recipient line with an existing restorer line to introduce the Rf allele. A series of backcrosses are then required to recover the genotype of the recipient line. Even after many generations of backcrosses some donor DNA linked to the Rf gene will remain, a phenomenon termed linkage drag; this donor DNA may carry deleterious traits and compromise the quality of the recipient strain.

Two CMS systems are proving to have some limited use in hybrid canola seed production. The Polima or pol cytoplasm is capable of conferring male sterility on many canola cultivars, and effective restorer lines, possessing dominant alleles at a single nuclear restorer locus, have been identified. The cost-effectiveness of hybrid production using this system is limited by the fact that pol-induced male sterility tends to be incomplete or "leaky", especially when the female line is exposed to warmer growing conditions. As a result, pol hybrid seed may be contaminated with CMS seeds that result from self-pollination of the female line. As these CMS plants are male sterile and do not spontaneously set seed, their presence can considerably lower the overall yield of the "hybrid" mixture. A second CMS system is based on the use of a hybrid cytoplasm in which the male sterility determinant is derived from a radish cytoplasm termed Ogura or ogu. Male sterility conferred by the ogu cytoplasm is complete. Restorer lines for this system, which were developed by intro-gressing a single radish restorer gene (which we designate here as Rfo) into *Brassica napus*, have recently become available, but the development of restorer lines is hampered by "linkage drag" between the restorer gene and genes that have a negative effect on seed quality.

It would be highly desirable to be provided with methods for enhancement of naturally occurring cytoplasmic male sterility and for restoration of male fertility and uses thereof in hybrid crop production.

SUMMARY OF THE INVENTION

One aim of the present invention is to provide methods for enhancement of naturally occurring cytoplasmic male sterility and for restoration of male fertility and uses thereof in hybrid crop production.

In accordance with the present invention there is provided a method for enhancing naturally occurring cytoplasmic male sterility in plants which comprises the steps of:
  a) introducing into the nucleus of a plant cell a gene construct essentially consisting of a sequence encoding a mitochondrial transit peptide fused upstream of and in frame with, at least one of, an unedited form of atp6 gene and an orf224 gene of *Brassica napus* mitochondria;
  b) selecting for plant cells that have acquired the gene construct in step a); and
  c) inducing regeneration of selected plant cells to produce a mature plant.

In accordance with the present invention there is also provided a method for restoration of male fertility to cytoplasmic male sterile plants which comprises the steps of:
  a) introducing into the nucleus of a plant cell a gene construct essentially consisting of a sequence encoding a mitochondrial transit peptide fused upstream of and in frame with an edited form of a normal mitochondrial gene that is co-transcribed with an unusual CMS-associated mitochondrial gene;
  b) selecting for plant cells that have acquired the gene construct in step a); and
  c) inducing regeneration of selected plant cells to produce a mature plant.

The preferred plant is *Brassica napus*.

Preferably, step b) is effected using a plant transformation vector.

In accordance with the present invention there is also provided a method for restoration of male fertility to polima cytoplasmic male sterile *B. napus* which comprises the steps of:
  a) introducing into the nucleus of a *B. napus* plant cell a gene construct essentially consisting of a sequence encoding a mitochondrial transit peptide fused upstream of and in frame with an edited form of an atp6 gene of *B. napus* mitochondria;
  b) selecting for plant cells that have acquired the gene construct in step a); and
  c) inducing regeneration of selected plant cells to produce a mature plant.

Our results have implications with respect to the practical implementation of pol CMS for the production of hybrid canola and other Brassica crops. The introduction, into pol CMS plants, of genetic constructs that allow the targeting of the product of the edited form of the Brassica atp6 gene to the mitochondria represents a new type of process by which male fertility restored plants can be recovered. This should allow the production of new pol CMS restorer lines in a single step, through plant transformation. This would represent a considerable savings in time and money over the conventional plant breeding methods for generating such lines, which is at present, the only way in which these lines can be generated. In addition, the introduction of constructs that allow the targeting of the products of the unedited form of the atp6 gene or orf224 into the mitochondria to produce plants with enhanced male sterility represents a process through which new pol CMS lines with enhanced maintenance of male sterility could potentially be produced. As mentioned above, the leakiness of pol male sterility is the major impediment to its more widespread use in hybrid canola production and there is no effective means of addressing this. It is also possible that these processes could represent examples of a more general strategy for the production of varieties that enhance the maintenance or that restore CMS in other CMS systems and with other plant species.

BRIEF DESCRIPTION OF THE DRAWINGS

FIG. +1 illustrates the use of cytoplasmic male sterility (CMS) in hybrid seed production;

FIG. 2A shows complete flowers of pol CMS Westar plants (left) and pol CMS Westar plants transformed with the mas2'/A9-A6e construct (note the increased size of the petals in the transgenic plant);

FIG. 2B shows complete flowers of partially male sterile transgenic plants obtained by introducing AP3/A9-A6u into Westar, plants (nap) (left) and male fertile Westar (nap) (note the decreased pigmentation of the petals of the transgenic flower);

FIG. 2C shows flowers with petals and sepals removed of pol CMS Westar (left) and pol CMS Westar transformed with the mas2'/A9-A6e construct (note the increased size of the stamens and the more highly developed anthers in the transgenic plant);

FIG. 2D shows flowers (with petals and sepals removed) of partially male sterile transgenic plants obtained by introducing AP3/A9-A6u into Westar (nap) (left) and male fertile Westar (nap) (note the reduction in anther size in the transgenic plant);

FIG. 2E shows complete flowers of (left to right) pol CMS Westar, male sterile transgenic plant 40-8 obtained by introducing the AP3/A9-ORF construct into male fertile Westar, (nap), and male fertile Westar (nap);

FIG. 2F shows the flower of transgenic plant 40-8 with petals and sepals removed (note that the four inner stamens have been transformed into carpels);

FIG. 2G shows complete flowers of the partially fertile transgenic plant 40-10 obtained by introducing the AP3/C4-ORF construct into a male fertile Westar (nap) (left); a flower of the recipient strain Westar (nap) is shown on the right (Note the reduction in petal size of the transgenic plant);

FIG. 2H shows flowers with petals and sepals removed from transgenic plant 40-10 and male fertile Westar (nap);

FIG. 2I shows complete flowers of pol CMS Westar (left) and a partially fertile transgenic plant obtained by introducing the AP3/A9-A6e construct into pol CMS Westar (note the increased petal size of the transgenic plant);

FIG. 2J shows flowers with petals and sepals removed of pal CMS Westar (left) and a partially fertile transgenic plant obtained by introducing the AP3/A9-A6e construct into pol CMS Westar (note the increased size of the stamens and anthers in the transgenic flower);

FIG. 5 illustrates the use of the AP3/C4-ORF construct to enhance pol cytoplasmic male sterility in *B. napus*.

DETAILED DESCRIPTION OF THE INVENTION

Figure 1:
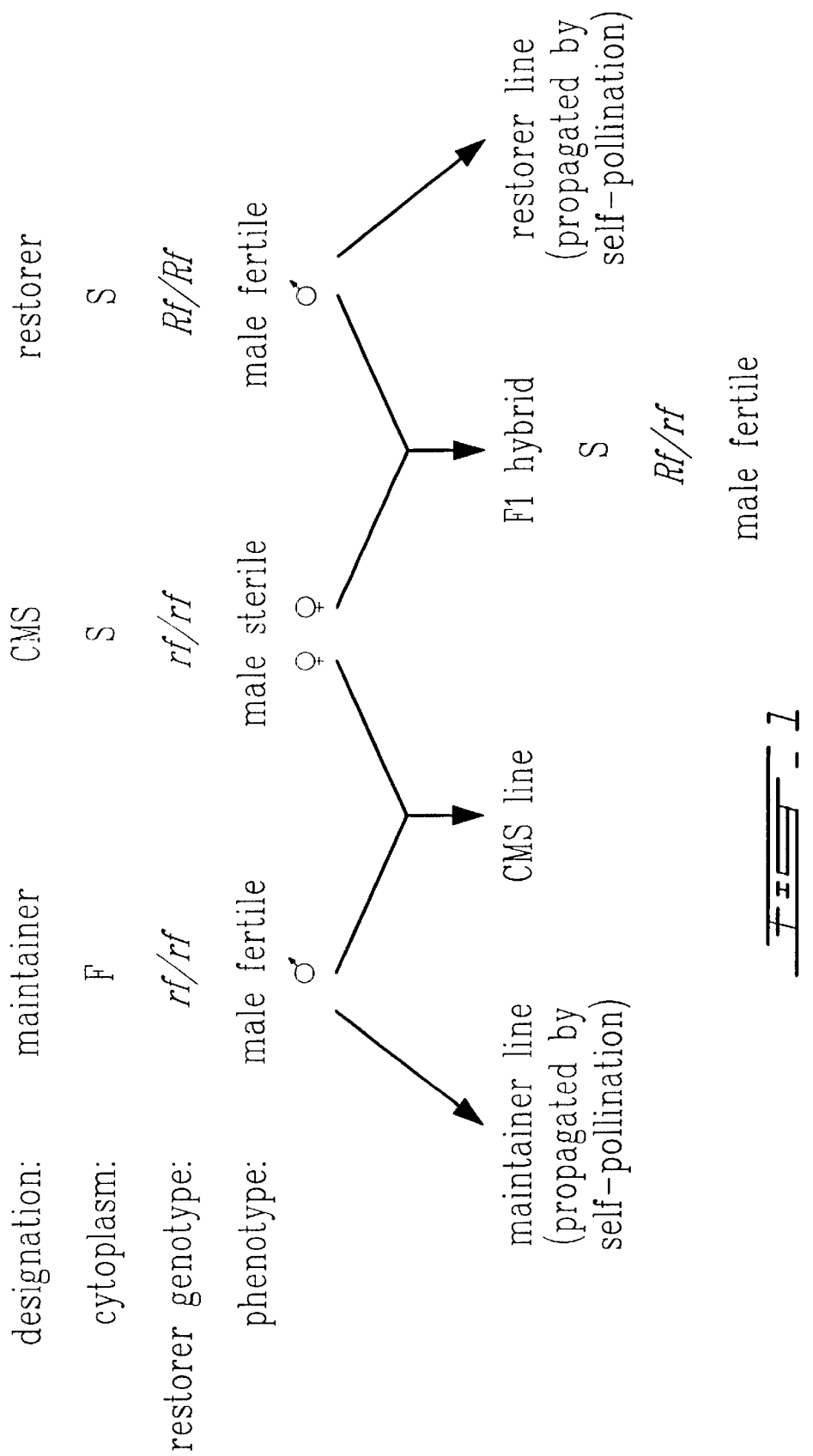

This invention provides a method for the development of maintainer and restorer lines through genetic engineering. The invention specifically relates to the pal CMS system of canola (*Brassica napus, campestris*). However, the method could, in principle, be used to modify the pollen production capacity of such lines for other CMS systems in canola and CMS systems in a large number of other crops.

This invention is based on research into the molecular basis of cytoplasmic male sterility (CMS) in canola (*Brassica napus* L.) that had been conducted in my laboratory between 1987 and 1993. Analysis of Brassica mitochondrial genome organization and expression had shown that the polima or pol form of *B. napus* CMS is correlated with expression of a mitochondrial gene region that contains a chimeric gene, orf224, that is co-transcribed with a normal mitochondrial gene, atp6 (Singh, M. P. and Brown, G. G. (1991). The Plant Cell 3, 1349–1362; Bonen, L. and Brown, G. G. (1993). Can. J. Bot. 71, 645–660). We hypothesized that pol CMS is due to a mitochondrial dysfunction that results either from (i) the presence of the ORF224 protein in the mitochondrial membrane, or (ii) from a possible deficiency in the ATP6 protein that might be caused by interference of orf224 in atp6 translation.

The proteins of the mitochondrion have a dual genetic origin. Some of these proteins, perhaps 10% or so, including those that specify CMS, are encoded in mtDNA, while others are encoded in nuclear DNA. Proteins encoded in mtDNA are synthesized on mitochondrial ribosomes, and remain within the mitochondrion. Nuclear-encoded mitochondrial proteins are synthesized as pre-cursors that usually contain an additional stretch of amino acids at the N-terminus called the transit peptide or presequence. This transit peptide serves to direct the protein to the mitochondrion. It is removed by a protease once the protein is inside the mitochondrion. If the DNA sequence for a protein normally encoded in mtDNA is fused to the DNA sequence of a mitochondrial transit peptide, and the resulting construct is introduced into and expressed in the nucleus, the resulting precursor protein can be imported into the mitochondrion and the final product can function in the same manner as the mitochondrially made form.

We reasoned that if hypothesis (i) was correct, then we might be able to confer male sterility on male fertile plants by expressing DNA constructs that would allow a nuclear-encoded, cytoplasmically translated ORF224 protein to be targeted to the mitochondria. Similarly, we reasoned that if hypothesis (ii) was correct, we might be able to restore male fertility to pol CMS plants by expressing DNA constructs that would permit a nuclear-encoded, cytoplasmically translated form of the ATP6 protein to be targeted to the mitochondria. If the constructs altered male sterility/fertility, then the orf224 transgenes could be viewed as synthetic maintainers of male sterility, while the atp6 transgenes could be viewed as synthetic restorers of male fertility. A further complication to these hypotheses came from the observations that both orf224 and atp6 transcripts are, like most plant mitochondrial transcripts, edited (Stahl R. et al. (1994) Nucleic Acids Res 22, 2109–2113). Plant mitochondrial transcript editing involves the conversion of specific C residues in an mRNA molecule to U residues which alters the amino acid sequence of the encoded protein (the edited mRNA codes for the functional form of the protein). Both the atp6 and orf224 transcripts are edited at a single site, resulting, in each case, in a single change in amino acid sequence. Since expression, in the nucleus, of a DNA construct that allowed targeting of an unedited wheat ATP9 protein to mitochondria conferred male sterility on transgenic tobacco plants (Hernould, M. et al. (1993). Proc. Natl. Acad. Sci. U.S.A. 90, 2370–2374), it seemed possible that expression/targeting of an unedited Brassica ATP6 protein could also cause male sterility and act as a synthetic maintainer gene.

Synthetic restorers of this type could, in principle, be used to create new restorer lines by genetic transformation. This would circumvent a lengthy and costly plant breeding exercise by which these lines are currently developed. The availability of synthetic maintainer genes might allow the generation of lines through plant transformation that could completely maintain pol sterility. Such lines currently do not exist, and this technology would therefore effectively remove the final barrier to yield enhancement by pol based canola hybrids. Finally, it is possible, even likely, that analogous strategies could be used to generate synthetic restorer and maintainer lines for crops other than canola and hence that a global strategy for genetically engineered maintenance and restoration of CMS could be developed. Evidence that Nuclear-encoded Mitochondrial Targeted Forms of the ATP6 and ORF 224 Proteins can act as Synthetic Restorer and Maintainer Genes, Respectively To begin to address these possibilities we fused DNA corresponding to the edited (A6e) and unedited (A6u) forms of the atp6 coding sequence to DNA coding for either of two mitochondrial targeting presequences, yeast COX4 (C4) or Neurospora ATP9 (A9). Similar constructs were prepared by fusing the same presequences to the unedited form of orf224 (ORFu). These sequences were joined, at their 5' end, to the mas2' promoter (van der Leegt-Plegt, L. M. et al. (1992). Plant Cell Reports 11, 20–24) and at their 3' end to a polyadenylation signal for the Cauliflower Mosaic Virus 35S RNA. The resulting constructs were introduced into *B. napus* cotyledons by Agrobacterium-mediated transformation (Moloney, M. et al. (1989). Plant Cell Rep. 8, 238–242). We were not able to regenerate plants into which the ORFu constructs had been introduced. Three of the transgenic plants we recovered after introducing the A9/A6u construct into fertile *B. napus* cv Westar were partially male sterile, while the single plant that we recovered after introducing the A9/A6e construct into sterile pol CMS *B. napus* was partially male fertile. This suggested that the construct expressing the unedited form of atp6 was acting as a sterility-inducing or maintainer gene, while the edited form was acting as a pol fertility restorer. Unfortunately, we were unable to recover seed from any of the plants expressing either construct, and so it was not possible to show that the changes in fertility/sterility could be genetically transmitted to subsequent plant generations or to confirm that the phenotypes resulted from transgene expression.

More recent research focused on the assembly of constructs in which a developmentally regulated promoter, derived from the APETALA3 (AP3) gene of *Arabidopsis thaliana* (Jack, T. et al. (1994) Cell 76, 703–716), was used to drive expression of atp6 and orf224 constructs. AP3 was chosen as a tissue specific promoter because it is expressed very early in the development of the stamen (as well as the petal). Previous data have indicated that the arrest in pollen development associated with the pol CMS is premeiotic and hence occurs early in stamen development; we therefore felt that to offset or mimic the pol CMS phenotype it would be necessary to express the constructs early in stamen development. Subsequent constructs that have been completed or are currently being assembled include one in which the "constitutive" mas2' promoter has been used for expression. All the constructs were inserted into a binary transformation vector, which has been optimized for efficient transformation in Brassica, and introduced into plants through the cotyledon transformation procedure. A summary of the constructs we have assembled, and the phenotypes of the transgenic plants we have recovered are indicated in Table 1, below.

Figure 2:
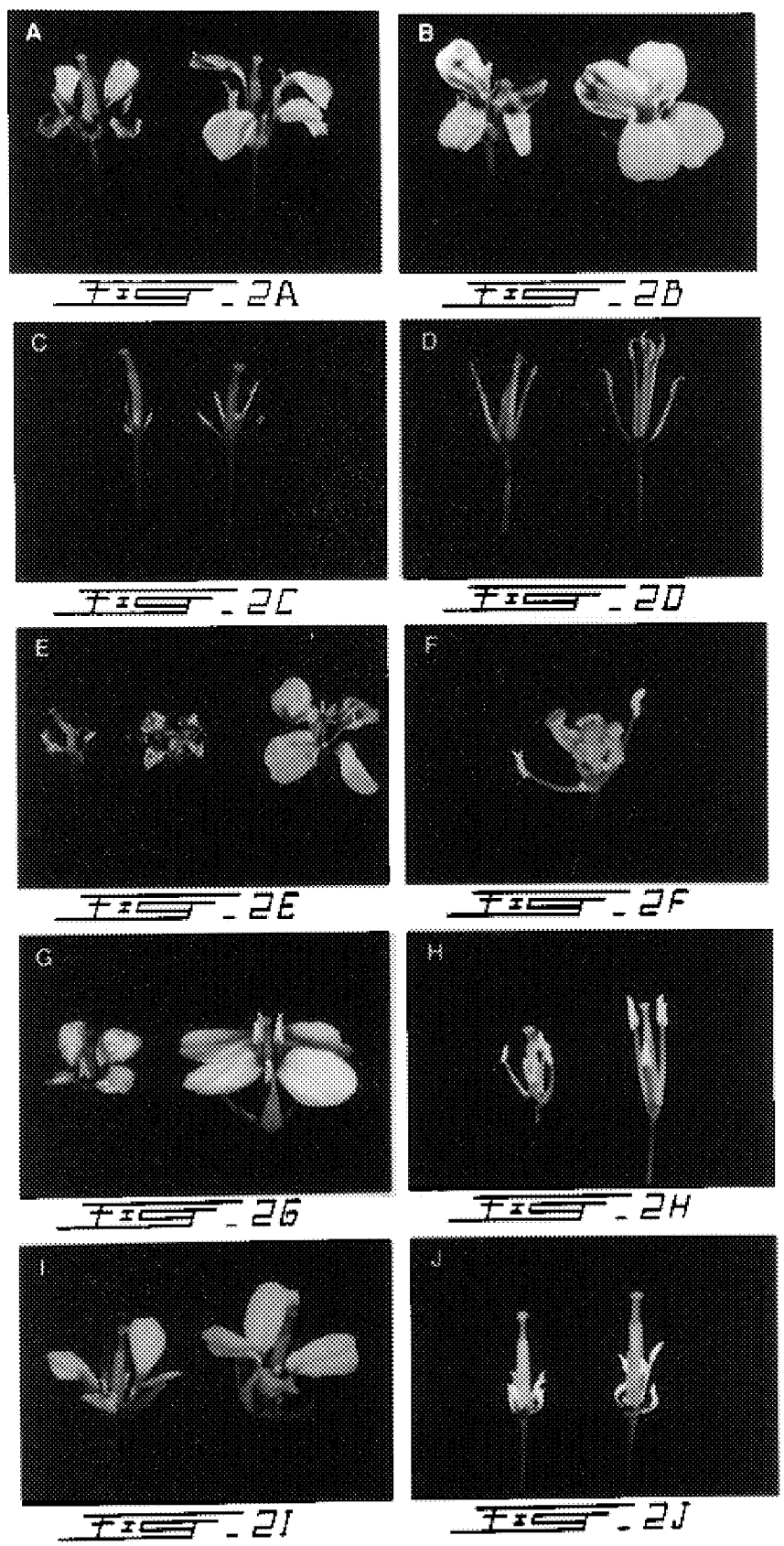
FIGS. 2A–2J illustrate the flowers of fertile, pol CMS and transgenic *B. napus* cv. Westar plants.

The data of Table 2 indicates the frequencies with which various constructs induced changes in male sterility or fertility in transgenic plants. Some of the changes observed in male fertility/sterility and floral structure in the transgenic plants are shown in FIG. 2.

The flowers shown on the left side of FIG. 2A and the right side of FIG. 2B are from pol CMS Westar and fertile Westar (nap) plants, respectively. The Figures beneath each of these (2C and 2D, respectively) show flowers from the same plants with the petals and sepals removed. As is evident in these figures, the stamens and petals of pol CMS plants are considerably smaller than those of westar (nap) flowers. Under the controlled growing conditions we have employed (20°, 16 h day, 15°, 8 h night), the stamens that form on flowers of young pol CMS plants are considerably less than half the height of the pistil, do not develop fully formed anthers and shed only small amounts of pollen.

TABLE 2

Numbers of transgenic plants with modified male fertility/sterility

| Construct | Recipient plant | Fertile[1] | Semi-fertile[2] | Semi-sterile[3] | Sterile[4] |
|---|---|---|---|---|---|
| AP3/A9-ORF | Westar (nap) | 6 | 3 | 1 | |
| AP3/C4-ORF | Westar (nap) | 5 | 5 | 2 | |
| AP3/A9-A6e | pol CMS Westar | | | 5 | 2 |

TABLE 1

Genetic constructs and corresponding phenotypes of transgenic plants

| Construct[1] | Introduced into | Kan[R] plants recovered | Confirmed transgenic[2] | Phenotype(s) of confirmed transgenic plants |
|---|---|---|---|---|
| AP3/C4-ORF[3] | fertile Westar (nap) | 17 | 12 | Variable male sterility ranging from near complete sterility (2 plants) to complete fertility (most plants); some plants show alterations in floral organ number, morphology & identity |
| AP3/A9-ORF | fertile Westar (nap) | 21 | 7 | Variable male sterility ranging from near complete sterility (1 plant) to complete fertility (most plants); some plants show alterations in floral organ number, morphology & identity |
| AP3/A9-A6e | male sterile Westar (pol) | 9 | 7 | All plants partially male fertile; stamen and petal size intermediate between fertile Westar (nap) and Westar (pol) CMS plants |
| AP3/A9-A6u | fertile Westar (nap) | 20 | 9 | Most plants male fertile with some flowers partially sterile; some plants display reduced stamens; pale yellow petals; changes in whorl identity and/or organ number. |
| mas2'/A9-A6e | male sterile Westar (pol) | 22 | 16 | Most plants partially male fertile; stamen and petal size intermediate between fertile Westar (nap) and Westar (pol) CMS plants; some plants show changes in floral whorl identity; elongated inflorescence and vegetative internodes. |
| AP3/GUS | Westar (nap) | 13 | 9 | Identical to Westar (nap); GUS expression observed at base of petals and stamens, as expected |

[1]Construct elements presented in sequence: promoter/presequence-coding sequence; AP3, Arabidopsis APETELA3 promoter; C4, yeast COX4 presequence; A9, Neurospora ATP9 presequence; ORF, edited orf224 coding sequence; A6e, edited atp6 coding sequence; A6u, unedited atp6 coding sequence.
[2]Confirmed by Southern blot analysis using a probe derived from the NPTII gene.
[3]Epitope-tagged edited atp6 coding sequence fused to the A9 presequence.
[4]Edited atp6 coding sequence, no targeting presequence.

TABLE 2-continued

Numbers of transgenic plants with modified male fertility/sterility

| Construct | Recipient plant | Fertile[1] | Semi-fertile[2] | Semi-sterile[3] | Sterile[4] |
|---|---|---|---|---|---|
| AP3/A9-A6u | Westar (nap) | 9 | | 6 | |
| mas2'/A9-A6e | pol CMS Westar | | 1 | 8 | 10 |

[1]Indistinguishable from Westar (nap)
[2]Reduced pollen release in comparison to Westar (nap); filled seed pods obtained upon selfing
[3]Minimal pollen release; poor seed set upon selfing
[4]Few or no seeds obtained upon selfing; several mas2'/A9-A6e plants produced significant pollen but failed to set seed and hence appear to be female and male sterile.

As indicated in Tables 1 and 2, in about half of the transgenic plants we recovered, AP3-driven expression of the edited orf224 coding sequence, fused to either targeting presequence, proved capable of reducing male fertility and inducing changes in floral morphology in Westar (nap) plants. The degree of sterility, as assessed by the amount of pollen visible on the anthers of newly opened flowers, as well as the nature of other floral abnormalities, varied somewhat among different transgenic plants and occasionally, to a much smaller degree, among the different inflorescence branches of individual plants. There was no apparent difference between the COX4 (C4) and ATP9 (A9) presequence constructs in either the conferred phenotype or the frequency with which male sterility was induced. Some indication of the phenotypes obtained can be seen in FIGS. 2E–H, which show flowers from the transgenic plants in which a change in pollen production was observed. In these plants, the sizes of the petals and stamens as well as the amount of pollen produced were reduced in comparison to Westar (nap), although not to the extent to which they are reduced in pol CMS plants. The most extreme phenotype was observed with the transgenic plant 40-8, an A9-ORF transformant (FIGS. 2E & 2F). In the flowers of this plant, the four inner stamens were converted into carpel-like structures and the anthers that formed on the two outer stamens remained pale yellow and shed only very small amounts of pollen.

We assessed the capacity of individual plants to set seed upon self fertilization as a practical measure of their male/female fertility. To self plants we usually place a crossing bag over an inflorescence and gently tap it to promote pollination. In the case of normal male fertile plants, all the seed pods within the bag will be completely filled; pol CMS plants produce no, or very few seeds under these conditions. When we attempted to self transgenic plants expressing AP3/A9-ORF or AP3/C4-ORF constructs in this manner, we found that in one case no seeds were produced (transgenic plant 40-8, FIG. 2), and, in several other cases, only a few seeds, were obtained. Those plants which displayed a marked reduction in seed set, but retained the capacity to produce some pollen were designated as "semi-sterile" (Table 2). In total 3 of the 22 confirmed transgenic ORF plants were semi-sterile by this test.

Expression of the unedited form of the atp6 gene (A6u) fused to the ATP9 presequence, when driven by the AP3 promoter, also proved capable of reducing the fertility of Westar (nap) plants (Table 1). Slightly fewer than half of the recovered transgenic plants expressing this construct showed a reduction in male fertility (Table 2). In general, however, the reduction of male sterility, according to the capacity to set seed, was more pronounced than with the ORF constructs. All the transgenic plants which showed a phenotype were classified as semi-sterile. Most of the plants with reduced fertility also possessed small, pale yellow petals. The semi-sterile phenotype displayed by one of the AP3/A9-A6u plants is shown in FIGS. 2B and D. We have also found that constructs of this type, as well as the ORF constructs and a third type of AP3/A9-A6 construct, AP3/A9-A6ep, in which the ATP6 coding sequence is interrupted by a sequence encoding a small peptide, can enhance the sterility of pol CMS plants. pol CMS plants normally produce a small amount of pollen; pol CMS plants expressing AP3/A9-A6u shed no pollen.

As shown in FIGS. 2I and J, AP3-driven expression of the edited atp6 construct in pol CMS plants caused a change in phenotype consistent with the prediction that it acts as a synthetic restorer gene. Flowers on these transgenic plants had petals and stamens intermediate in size between those of pol CMS and fertile Westar (nap) plants. The anthers of these flowers developed small, yellow anthers that produced significant amounts of pollen, although not as much as male fertile Westar (nap) plants (Table 1). All the transgenic plants displayed an altered phenotype (Table 2), although the amount of pollen produced varied slightly from plant to plant. These plants were all capable of producing seed upon bagging of the inflorescence; two of the plants produced only small amounts of seed, while the five remaining plants produced filled pods without bagging or any other type of intervention. These latter 5 plants can therefore be regarded as being fertility restored in the full functional sense of the term.

Figure 3:
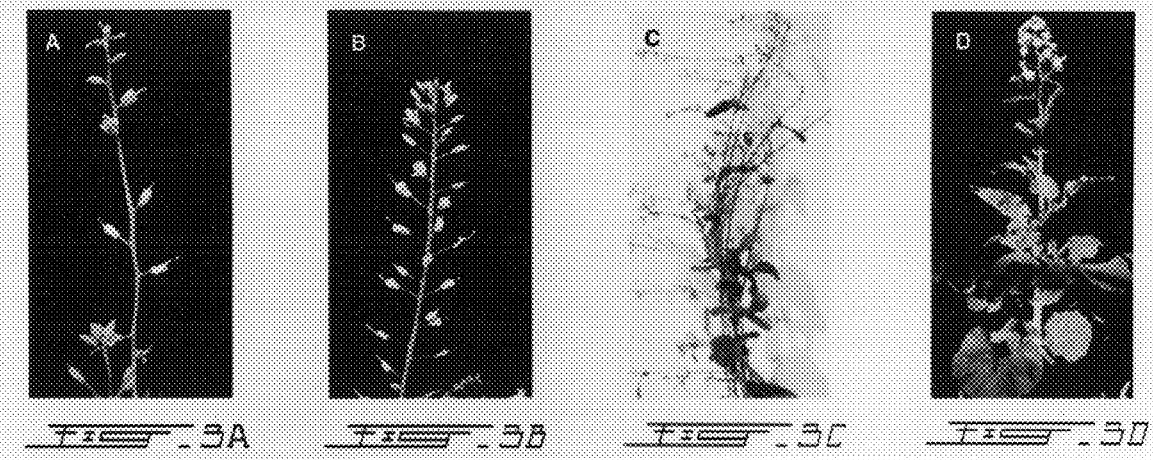
FIGS. 3A–3D illustrate phenotypic changes accompanying mas2'-driven expression of A9-A6e in pol CMS Westar; A: Transgenic plant inflorescence; B: pol CMS Westar inflorescence; C: entire transgenic plant; D: pol CMS Westar plant (Note the increased size of the inflorescence and vegetative internodes in the transgenic plant)

We also assessed the capacity of the A9-A6e construct to induce male fertility in pol CMS plants when expressed using the "constitutive" promoter mas2'. Six of the transgenic plants we recovered possessed flowers that were virtually identical to those produced by AP3/A9-A6e plants (FIGS. 1A & 1C). The remaining plants produced either smaller amounts or virtually no pollen. Only one of the pollen producing plants was capable of forming significant numbers of seeds without being manually pollinated which suggests that the female fertility of the mas2'/A9-A6e plants is, in general, reduced. This is consistent with previous results obtained using constructs of this type in which plants with fertile flowers that are incapable of setting seeds were recovered. A second feature of the plants we recovered is also consistent with our preliminary results: all the plants expressing A9-A6e from the mas2' promoter showed changes in vegetative growth. In particular, both vegetative and inflorescence internodes were longer than those of Westar (nap) or pol CMS Westar plants (FIG. 3). In some transgenic plants, leaf morphology was also affected. Similar changes were not observed in any of the plants in which the AP3 promoter was for expression. Thus, both the reduction in female fertility and other abnormalities result from the generalized expression of the fusion protein from the mas2' promoter.

The observation of similar types of sterility modifications in multiple independently transformed plants provides very strong support for our initial hypotheses, namely: (i) that constructs which allow targeting of the ORF224 or unedited ATP6 polypeptides to the mitochondria can confer sterility on male fertile plants and hence serve as synthetic maintainer genes; and (ii) that constructs which allow targeting of the edited ATP6 polypeptide to the mitochondria can serve as synthetic restorer genes. The data also indicates that to avoid deleterious effects on vegetative growth and female fertility, it is necessary to express these constructs using a tissue specific or inducible promoter. The analysis of the R1 progeny of the RO plant (a plant recovered from the transformation—regeneration protocol) the C4-ORF-expressing plant 40-8 (see above) has provided compelling evidence that the phenotypes observed are inheritable and due to the transgene. We raised 20 of these plants to maturity. A range of floral phenotypes was evident, from the extreme abnormalities of the parental plant (where only two very sterile anthers form and the remaining four anthers are converted to pistil-like organs), to the partial male fertility observed in many of the RO plants that express this construct. All the R1 progeny plants contained the transgene, suggesting that the original 40-8 RO plant may have had more than one copy of the gene. This would further indicate that the degree of sterility expressed is dependent on gene dosage. This gene dosage effect provides an additional means of modifying the degree of sterility expressed by the transgenic plants.

In summary, our experiments represent the first case in which male sterility has been induced through the targeting of the products of mitochondrial ORFs (orf224 and the unedited atp6) in a homologous host plant, and the first time that Brassica genes have been used for this purpose. Our results also strongly suggest that the A9-A6e construct can serve as a fertility restorer gene for the pol CMS. This is the first case we are aware of in which a natural form of CMS has been suppressed by a synthetic gene construct.

Our results are consistent with experiments conducted by other researchers, who have found the expression/targeting of the protein products of a bean CMS-associated ORF (He, S. et al. (1996). Proc. Natl. Acad. Sci. U.S.A. 93, 11763–11768) or an unedited wheat ATP9 gene (Hernould, M. et al. (1993). Proc. Natl. Acad. Sci. U.S.A. 90, 2370–2374), in the heterologous recipient plant, tobacco, can induce male sterility. Interestingly, similar types of experiments with CMS-associated ORFs from maize and petunia have failed to result in the recovery of male sterile plants (Chaumont, F. et al. (1995). Proc. Natl. Acad. Sci. USA 92, 1167–1171; Wintz H. et al. (1995). Plant Mol Biol 28, 83–92). The frequency with which we recovered male sterile plants was higher than was observed for the bean ORF, and difficult to compare with the results using the unedited wheat ATP9 gene.

The present invention will be more readily understood by referring to the following examples which are given to illustrate the invention rather than to limit its scope.

EXAMPLE I

Use of the AP3/A9-A6e Construct as a Dominant Fertility Restorer Gene in *B. Napus*

Figure 4:
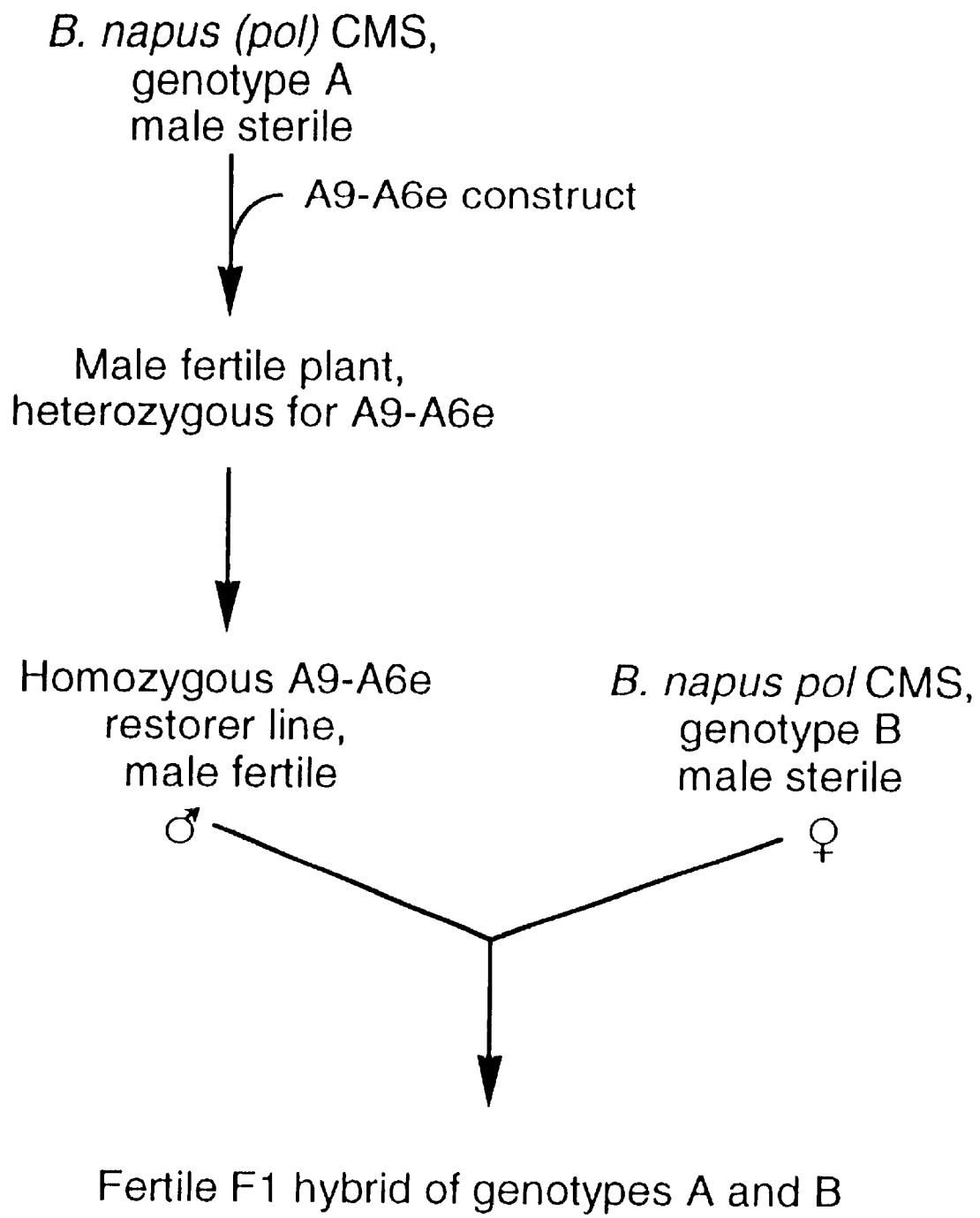
FIG. 4 illustrates the use of the AP3/A9-A6e construct as a dominant fertility restorer gene in *B. napus*.

In this example, outlined in FIG. 4, the A9/A6e construct is introduced by genetic transformation into the genome of a variety such as Westar which is normally sterilized by (pol) cytoplasm. The gene would be introduced into a pol cytoplasm line, and the resulting transgenic plants recovered are expected to be partially male fertile. This line is then self-fertilized to generate a partially male fertile restorer line that is homozygous for the A9/A6e transgene. This line could then be crossed with different pol CMS lines to generate fertility restored F1 hybrids.

EXAMPLE II

Use of the AP3/C4-ORF Construct to Enhance pol Cytoplasmic Male Sterility in *B. Napus*

The sterility induced by the pol cytoplasm on most *B. napus* genotypes is incomplete, especially at higher temperatures. Residual pollen production results in variable degrees of self-fertilization in the CMS line in a hybrid seed production operation. Plants raised from these seeds will not be hybrid and will have a reduced capacity themselves to set seed. These factors together can reduce, to a considerable extent, the yield of the "hybrid" seed batch. In this example, outlined in FIG. 5, the dominant sterility conferring properties of C4-ORF are employed to reduce or eliminate residual pollen production in the CMS line, and thereby enhance the percentage of hybrid seed recovered, and the hence yield of the hybrid seed batch. The C4-ORF construct is introduced by genetic transformation into a fully male fertile Westar (nap) line to produce a partially male fertile line that contains the C4-ORF transgene. This line is then self-fertilized to generate a partially male fertile maintainer line and is also crossed with a non-transformed line of the same nuclear genotype but with a pol cytoplasm, to generate a completely sterile pol CMS line that is heterozygous for C4-ORF.

This is backcrossed to the C4-ORF partially male fertile maintainer line to generate a completely male sterile pol CMS line that is homozygous for C4-ORF. This CMS line, when crossed to a pol restorer line, will produce a fertile F1 hybrid. The completely sterile pol CMS line is propagated by crossing it, as female, with the nap cytoplasm, partially male fertile transgenic C4-ORF maintainer line.

Although we have described a method for enhancing the sterility of a pol CMS plant using the AP3/C4-ORF construct, the AP3/A9-A6a and AP3/A9-A6ep constructs could also be used for this purpose, as the expression of each of these constructs results in completely male sterile pol CMS transgenic plants.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of reducing pollen production in plants, which comprises the steps of:
    a.) introducing into the nucleus of a plant cell a gene construct essentially consisting of a developmentally regulated promoter driving expression of a sequence encoding a mitochondrial transit peptide fused upstream of and in frame with an edited form of the orf224 gene of *Brassica napus* mitochondria, wherein said promoter is expressed early in stamen development;
    b.) selecting for plant cells that have acquired the gene construct in step a); and
    c.) inducing regeneration of selected plant cells to produce a mature plant with reduced pollen production.

2. The method of claim 1, wherein the plant is *Brassica napus*.

3. The method of claim 1, wherein step a) is effected using a plant transformation vector.

4. The method of claim 1, wherein said promoter is AP3.

5. The method of claim 1, wherein the plant is male fertile.

6. The method of claim 1, wherein the plant is partially male sterile.

7. A method of reducing pollen production in partially male sterile Brassica plants, which comprises the steps of:

a.) introducing into the nucleus of a plant cell a gene construct essentially consisting of a developmentally regulated promoter driving expression of a sequence encoding a mitochondrial transit peptide fused upstream of and in frame with an unedited form of the atp6 gene of *Brassica napus* mitochondria, wherein said promoter is expressed early in stamen development;

b.) selecting for plant cells that have acquired the gene construct in step a); and c.) inducing regeneration of selected plant cells to produce a mature plant with reduced pollen production.

8. The method of claim 7, wherein the plant is *Brassica napus*.

9. The method of claim 7, wherein step a) is effected using a plant transformation vector.

10. The method of claim 7, wherein said promoter is AP3.

* * * * *